(12) United States Patent
Averback

(10) Patent No.: US 12,090,191 B2
(45) Date of Patent: *Sep. 17, 2024

(54) METHOD OF ENHANCING THE THERAPEUTIC EFFICACY OF FEXAPOTIDE TRIFLUTATE IN TREATING LUTS

(71) Applicant: Nymox Corporation, Nassau (BS)

(72) Inventor: Paul Averback, Nassau (BS)

(73) Assignee: NYMOX CORPORATION, Nassau (BS)

(*) Notice: Subject to any disclaimer, the term of this patent is extended or adjusted under 35 U.S.C. 154(b) by 0 days.

This patent is subject to a terminal disclaimer.

(21) Appl. No.: 17/557,951

(22) Filed: Dec. 21, 2021

(65) Prior Publication Data

US 2022/0226424 A1    Jul. 21, 2022

Related U.S. Application Data

(63) Continuation of application No. 16/410,639, filed on May 13, 2019, now Pat. No. 11,298,400.

(51) Int. Cl.
| | | |
|---|---|---|
| A61K 38/00 | (2006.01) | |
| A61K 38/10 | (2006.01) | |
| A61P 13/08 | (2006.01) | |

(52) U.S. Cl.
CPC ............ *A61K 38/10* (2013.01); *A61P 13/08* (2018.01)

(58) Field of Classification Search
CPC ................................ A61K 38/10; A61P 13/08
See application file for complete search history.

(56) References Cited

U.S. PATENT DOCUMENTS

| | | | |
|---|---|---|---|
| 4,457,489 | A | 7/1984 | Gilmore |
| 6,924,266 | B2 | 8/2005 | Averback |
| 7,172,893 | B2 | 2/2007 | Rabinowitz et al. |
| 7,192,929 | B2 | 3/2007 | Averback |
| 7,241,738 | B2 | 7/2007 | Averback et al. |
| 7,317,077 | B2 | 1/2008 | Averback et al. |
| 7,408,021 | B2 | 8/2008 | Averback et al. |
| 7,745,572 | B2 | 6/2010 | Averback et al. |
| 8,067,378 | B2 | 11/2011 | Averback et al. |
| 8,293,703 | B2 | 10/2012 | Averback et al. |
| 8,569,446 | B2 | 10/2013 | Averback et al. |
| 8,716,247 | B2 | 5/2014 | Averback et al. |
| 9,243,035 | B2 | 1/2016 | Averback et al. |
| 2007/0237780 | A1 | 10/2007 | Averback |
| 2016/0215031 | A1 | 12/2016 | Averback |
| 2017/0020957 | A1* | 1/2017 | Averback ............ A61K 38/17 |
| 2017/0360885 | A1 | 12/2017 | Averback |
| 2018/0064785 | A1 | 3/2018 | Averback |
| 2018/0350355 | A1 | 9/2018 | Averback |

OTHER PUBLICATIONS

Kunit et al. An evidence-based review of NX1207 and its potential in the treatment of benign prostatic hyperplasia (Res Rep Urol. 2014; 6: 67-70) (Year: 2014).*
Peyronnet et al. Lower Urinary Tract Symptoms: What's New in Medical Treatment ?. (European urology focus 4 (2018) 17-24) (Year: 2018).*
Urology Care foundation accessed Dec. 13, 2022 at (https://urology. weillcornell.org/sites/default/files/aua_symptom_score_web.pdf) (Year: 2016).*
Shore et al. Fexapotide triflutate: results of long-term safety and efficacy trials of a novel injectable therapy for symptomatic prostate enlargement(World Journal of Urology (2018) 36:801-809). (Year: 2018).*
Neal Shore et al. North Central Section of the AUA 82nd Annual Meeting Sep. 24-27, 2008 Chicago. A Prospective Randomized Two Dose Level Comparison of Single-Injection Transrectal Intraprostatic NX-1207 and Finasteride in Men With Lower Urinary Tract Symptoms Due to Benign Prostatic Hype (Year: 2008).*
AUA- Shore et al. A prospective randomized two dose level comparison of single injection transrectal intraprostatic NX-1207 and Finasteride in men with lower urinary tract symptoms sue to BPH; (North Central section Am. Urol. Assoc, p. 4291, #2, 2008). (Year: 2008).*
Office Action dated Apr. 21, 2021, issued in corresponding U.S. Appl. No. 16/410,685 (13 pgs.).
Teachmesurgery, Lower Urinary Tract Symptoms, https:// teachmesurgery.com/urology/presentatiosn/lower-urinary-tract-symptoms/accessed on Apr. 16, 2021 (4 pgs.).
Shore et al. Efficacy and safety of fexapotide triflutate in outpatient medical treatment of male lower urinary tract symptoms associated with benign prostatic hyperplasia. 2019. Ther Adv Ural. 2019, vol. 11: 1-16 (Year: 2019) (Year: 2019).
Kunit et al. An evidence-based review of NX1207 and its potential in the treatment of benign prostatic hyperplasia. 2014. Res Rep Ural. 2014; 6: 67-70 (Year: 2014) (Year: 2014).
International Search Report and Written Opinion of the International Searching Authority dated Aug. 6, 2020 issued in corresponding International Application No. PCT/US2020/031592.
International Search Report and Written Opinion of the International Searching Authority dated Aug. 13, 2020 issued in corresponding International Patent Application No. PCT/US2020/031792 (13 pgs.).
Neal Shore et al., "The Potential for NX-1207 in Benign Prostatic Hyperplasia: an update for Clinicians", Therapeutic Advances in Chronic Disease (2011), 2(6) 377-383.

(Continued)

*Primary Examiner* — Aradhana Sasan
*Assistant Examiner* — Mercy H Sabila
(74) *Attorney, Agent, or Firm* — Pillsbury Winthrop Shaw Pittman, LLP

(57) ABSTRACT

Disclosed are methods of enhancing the therapeutic efficacy of Fexapotide Triflutate (TF) in treating LUTS, both irritative and obstructive, that include administering a composition comprising FT at least twice over a period spanning more than one year. The methods are capable of providing an enhanced therapeutic effect in treating nocturia, and in improving urinary flow, when compared to the therapeutic effect achieved by administration of the same or twice the total amount of FT administered.

14 Claims, No Drawings

Specification includes a Sequence Listing.

(56) References Cited

OTHER PUBLICATIONS

Anonymous: "Efficacy and Safety of a Single TRUS-guided Intraprostatic Injection of NX-1207 in Patients with LUTS Due to BPH—NCT02003742", ClinicalTrials.gov, Dec. 6, 2013, pp. 1-8, XP055712762, URL:http://clinicaltrials.gov/ct2/show/record/NCT02003742.
Karl-Erik Andersson, "Treatment of Lower Urinary Tract Symptoms: Agents for Intraprostatic Injection", Scandinavian Journal of Urology, 2013; 47: 83-90.
Non-final Office Action dated Feb. 13, 2020 issued in corresponding U.S. Appl. No. 16/410,685.
Neal Shore et al., "Fexapotide triflutate: results of long-term safety and efficacy trials of a novel injectable therapy for symptomatic prostate enlargement", World Journal of Urology (2018) 36: 801-809.
S. Altschul et al. "Basic Local Alignment Search Tool", J. Mol. Biol., 215: 403-410 (1990).
Humberto Carrillo et al., "The Multiple Sequence Alignment Problem in Biology", Siam, J. Applied Math., vol. 48, No. 5, Oct. 1988, pp. 1073-1082.
J. Couder et al., "Synthesis and Biological Activities of ψ(Ch2NH) Pseudopeptide analogies of the C-terminal Hexapeptide of neurotensin" Int. J. Peptide Protein Res., 41:181-184, 1993.
Alma Dalpozzo et al. "H-Gly-Hisψ(NHCO) Lys-OH, partially modified retro-inverso analogue of the growth factor Glycyl-L-histidyl-L-lysine with enhanced enzymatic stability", (1993), Int. J. Peptide Protein Res., 41:561-566.
J. Devereux, et al., "A Comprehensive set of Sequence Analysis Programs for the VAX", Nucleic Acids Research, 12(1): 387-395 (1984),.
E. J. Freireich et al., "Quantitative Comparison of Toxicity of Anticancer Agents in Mouse, Rat, Hamster, Dog, Monkey, and Man", Cancer Chemother. Rep., vol. 50, No. 4, pp. 219-244 (May 1966).
Steven Henikoff et al., "Amino Acid Substitution Matrices from Protein Blocks", Proc. Natl. Acad. Sci USA, 89:10915-10919, Nov. 1992.
Suresh I.S. Rattan et al., "Protein Synthesis: Posttranslational Modifications and Aging," Ann. N.Y. Acad. Sci. 663: 48-62 (1992).
Scientific Tables, Geigy Pharmaceuticals, Ardsley, N.Y. pp. 537-538 (1970).
Sam Seifter et al., "[47] Analysis for Protein Modifications and Nonprotein Cofactors", Methods in Enzymology, vol. 182 pp. 626-646 (1990).
Reyna J. Simon et al., "Peptoids: A modular approach to drug discovery", Proc. Natl. Acad. Sci. USA, vol. 89, pp. 9367-9371, Oct. 1992.
A. Sisto et al. in Rivier, J. E. and Marshall, G. R., "Biologically active retro-inverso analogs of thymopentin", Peptides, Chemistry, Structure and Biology, Escom, Leiden (1990), pp. 722-773.
Smith Craig C. et al., "Tritiated D-ala.sup. 1-Peptide T Binding", Drug Development Res., 15, pp. 371-379 (1988).
Gunnar Von Heijne, "Chapter 6, Sequence Similarities, Homologies, and Alignments", Sequence Analysis in Molecular Biology, p. 123-139 Academic Press, New York, N.Y. 1987.
Wold, F., "Posttranslational Protein Modifications: Perspectives and Prospects," pp. 1-12 in Posttranslational Covalent Modification of Proteins, B. C. Johnson, Ed., Academic Press, New York (1983).
Ruth Etzioni et al., "Asymptomatic Incidence and Duration of Prostate Cancer", Am J Epidemiol. Vol. 148, No. 8, pp. 775-785 (1998).

Roman Gulati et al., "What If I Don't Treat My PSA-Detected Prostate Cancer? Answers from Three Natural History Models", Cancer Epidemiol Biomarkers Prev; 20(5), pp. 740-750, May 2011.
Roberta Mazzucchelli et al., "Pathology of Prostate Cancer and Focal Therapy ('Male Lumpectomy')", Anticancer Research, vol. 29, pp. 5155-5162 (2009).
Chinyere Ibeawuchi et al., "Genome-Wide Investigation of Multifocal and Unifocal Prostate Cancer—Are They Genetically Different?" Int. J. Mol. Scl., vol. 14, pp. 11816-11829 (2013).
Philip Quann et al., "Current prostate biopsy protocols cannot reliably identify patients for focal therapy: correlation of low-risk prostate cancer on biopsy with radical prostatectomy findings", Int. J. Clin. Exp. Pathol., 3(4), pp. 401-407 (2010).
M.O. Dayhoff et al. "22 A Model of Evolutionary Change in Proteins", Atlas of Protein Sequence and Structure, vol. 5, supp. 3, pp. 345-352, (1978).
Hashim Uddin Ahmed et al., "Do Low-Grade and Low-Volume Prostate Cancers Bear the Hallmarks of Malignancy," www.thelancet.com/oncology, vol. 13, pp. e509-e517 (Nov. 2012).
Neal Shore et al., "The potential for NX-1207 in benign prostatic hyperplasia: an update for clinicians," Ther. Adv. Chronic Dis., 2(6), pp. 377-383 (2011).
Chun-Hou Liao et al., "Use of the International Prostate Symptom Score Voiding-to-Storage Subscore Ratio in Assessing Lower Urinary Tract Symptoms", Tzu Chi Medical Journal 26 (2014) pp. 61-63.
"Lower Urinary Tract Symptoms in Men", National Institute for Health and Care Excellence, published Sep. 18, 2013, 32 pgs. www.nice.org.uk/guidance/qs45.
"Lower Urinary Tract Symptoms in Men: Management", National Institute for Health and Care Excellence, published May 23, 2010, 24 pgs. www.nice.org.uk/guidance/cg97.
Neal Shore et al., "The Potential for NX-1207 in Benign Prostatic Hyperplasia: An Update for Clinicians", Therapeutic Advances in Chronic Disease, 2(6), 2011, pp. 377-383.
C.C.K. Ho et al., "Urinary Bladder Characteristics via Ultrasound as Predictors of Acute Urinary Retention in Men with Benign Prostatic Hyperplasia", Clin. Ter. 2014; 165(2), pp. 41-47.
Neal Shore et al., "Fexapotide Triflutate: Results of Long-Term Safety and Efficacy Trials of a Novel Injectable Therapy for Symptomatic Prostate Enlargement", World Journal of Urology (2018) 36, pp. 801-809.
Office Action dated Oct. 18, 2023, issued in corresponding Russian Patent Application No. 2021136424/14 with English translation (29 pgs.).
Office Action dated Oct. 31, 2023, issued in corresponding Russian Patent Application No. 2021136491/04 with English translation (25 pgs.).
Z.K. Gadzhieva et al., "Functional State of the Lower Urinary Tract in Men With Bladder Outlet Obstruction", Ural Medical Journal, 2018;(9): 43-51.
G.R. Kasyan et al., "Current Opportunities for Combination Treatment of Lower Urinary Tract Symptoms Due to Benign Prostatic Hyperplasia in Men", Research and Practice in Medicine, 2016, vol. 3, 2 pp. 37-44.
D.A. Kharkevich, "Farmakologiya [Pharmacology]", Tenth Edition, GEOTAR Media, 2010, p. 73 with English translation (6 pgs.).
G.G. Krivoborodov et al., "Alpha-Blockers for Lower Urinary Tract Symptoms in Benign Prostatic Hyperplasia", placed on the website in the Internet on Jan. 18, 2016. URL:https://remedium.ru/doctor/urology/primenenie-alfa-blokatorovdlya-ustraneniya-simptomov-sostorony-nizhnikhmochevyvodyashchikh-putey-/).

\* cited by examiner

SEQUENCE LISTING

<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Ile Asp Gln Gln Val Leu Ser Arg Ile Lys Leu Glu Ile Lys Arg Cys
1               5                   10                  15

Leu

METHOD OF ENHANCING THE THERAPEUTIC EFFICACY OF FEXAPOTIDE TRIFLUTATE IN TREATING LUTS

CROSS-REFERENCE TO RELATED APPLICATIONS

This application is a continuation of U.S. patent application Ser. No. 16/410,639, filed May 13, 2019, which application is incorporated herein in its entirety by reference.

SEQUENCE LISTING

The instant application contains a Sequence Listing which has been submitted electronically in ASCII format and is hereby incorporated by reference in its entirety.

BACKGROUND

1. Field of the Embodiments

The embodiments include methods of enhancing the therapeutic efficacy of fexapotide triflutate ("FT") by administering compositions containing FT at least twice over a period of time in which the treatment is more effective than administering a single dose of FT in an amount of 1×, 2×, or 4× the individual amount administered each time. More particularly, the embodiments include methods of enhancing the therapeutic efficacy of FT in treating LUTS by first administering FT, and subsequently administering FT at least one more time at least one year after the first administration.

2. Description of Related Art

The essence of many medical treatments and procedures involves the removal or destruction of harmful or unwanted tissue. Examples of such treatments include the surgical removal of cancerous or pre-cancerous growths, the destruction of metastatic tumors through chemotherapy, and the reduction of glandular (e.g. prostate) hyperplasia. Other examples include the removal of unwanted facial hair, the removal of warts, and the removal of unwanted fatty tissue.

Benign prostatic hyperplasia (BPH) is common in older men, with symptoms that impact quality of life, including interference with activities and perception of well-being. BPH can be progressive, with risk of urinary retention, infections, bladder calculi, and renal failure. Although many men with mild to moderate symptoms do well without intervention, bothersome symptoms and complications can progress in others, leading to medical therapy or surgery.

Benign Prostatic Hyperplasia (BPH) is a histologic diagnosis that refers to the nonmalignant proliferation of smooth muscle and epithelial cells of the prostate. Lee C, et al., "Intrinsic and extrinsic factors controlling benign prostatic growth," Prostate, 1997; 31:131-138; Auffenberg G B, et al., "Established medical therapy for benign prostatic hyperplasia," *Urol Clin North Am*,. 2009; 36:443-459. The exact etiology is unknown. The progression of BPH can lead to benign prostatic enlargement (BPE), which is determined by the size of the prostate (pathologic). Approximately 50% of men with histologic BPH develop BPE. BPE may eventually cause bladder outlet obstruction (BOO), which is also termed benign prostatic obstruction (BPO) if associated with BPE. BOO and BPO are determined with urodynamic measures. Some patients may present with BPE but not have significant LUTS, while other patients may present with LUTS and have a significant reduction in QoL but not have BPE and.or BPH. Park, H. J., et al., "Urinary Tract Symptoms (LUTS) Secondary to Benign Prostatic Hyperplasia (BPH)., *World J. Mens Health*, No. 31(3), 193-207 (2013).

Lower urinary tract symptoms (LUTS) in men with prostate enlargement are generally classified into 2 main types of symptoms: 1. "irritative" also referred to as "storage" symptoms; and 2) "obstructive" also referred to as "voiding" symptoms. The irritative/storage symptoms include urgency of need to urinate, higher frequency, and nocturia (need to urinate more frequently after going to sleep at night). The obstructive voiding symptoms include weak urinary stream, need to push or strain to evacuate the urine, sensations of incomplete emptying after urination, and stopping and starting several times during the course of voiding. Amongst the most bothersome of these symptoms is nocturia which causes poor sleep quality and other problems such as chronic fatigue and bother to spouses.

The United States and Europe have established guidelines to assist physicians in the treatment of LUTS, BPH, and LUTS/BPH. Oelke M, et al., European Association of Urology, *Eur. Urol.* 2013 July; 64(1):118-40. The guidelines discuss treatment options varying from watchful waiting (WW), for men presenting with symptoms but are not bothered enough to need medication or surgical intervention, to drug treatments, to surgical intervention. Drug treatment guidelines have included the use of alpha-blockers (alpha-adrenergic antagonists), 5-alpha-reductase inhibitors (5ARIs), antimuscarinics (anticholinergics), a PDE5 inhibitor (tadalafil), combination therapies, and vasopressin analogues. The use of combination therapies such as an alpha-blocker with a 5ARI or antimuscarinic also have been recommended.

Prostate surgery such as transurethral resection of the prostate is indicated in men with absolute indications or drug treatment-resistant BPH, LUTS, or acute urinary retention (AUR). Indications for surgery include severe conditions such as urinary retention, gross hematuria, urinary tract infection, and bladder stones. Minimally invasive treatments include transurethral microwave therapy and transurethral needle therapy. An alternative to catheterization for men unfit for surgery include prostate stents. Despite the various available treatment options, there remain unmet medical needs for effective and safe agents to treat these bothersome symptoms, some of which may be caused by prostate enlargement, which can lead to more serious problems such as chronic urinary tract infections, incontinence, acute and chronic urinary retention, and renal failure.

Some agents known to have the ability to destroy and hence either facilitate the removal of or inhibit the further growth of harmful or unwanted cells and tissue are disclosed in U.S. patent application Ser. No. 14/808,713, filed Jul. 24, 2015, entitled: METHODS OF REDUCING THE NEED FOR SURGERY IN PATIENTS SUFFERING FROM BENIGN PROSTATIC HYPERPLASIA; U.S. patent application Ser. No. 14/606,683, filed Jan. 27, 2015, entitled: METHOD OF TREATING DISORDERS REQUIRING DESTRUCTION OR REMOVAL OF CELLS, U.S. application Ser. No. 14/738,551, filed Jun. 12, 2015, entitled: COMBINATION COMPOSITIONS FOR TREATING DISORDERS REQUIRING REMOVAL OR DESTRUCTION OF UNWANTED CELLULAR PROLIFERATIONS, U.S. patent application Publication Nos. 2007/0237780 (now abandoned); 2003/0054990 (now U.S. Pat. No. 7,172,893); 2003/0096350 (now U.S. Pat. No. 6,924,266); 2003/0096756 (now U.S. Pat. No. 7,192,929); 2003/0109437

(now U.S. Pat. No. 7,241,738); 2003/0166569 (now U.S. Pat. No. 7,317,077); 2005/0032704 (now U.S. Pat. No. 7,408,021); and 2015/0148303 (now U.S. Pat. No. 9,243, 035), the disclosures of each of which are incorporated by reference herein in their entirety.

One of the agents disclosed in these documents is fexapotide triflutate, or FT. FT has been shown to reduce prostate glandular cells. In controlled clinical studies for treating BPH, and some of its symptoms, the overall improvements with FT were greater than placebo treatments after long-term observations.

There exists a need for treatments that can improve LUTS without the risks and side effects of conventional drug therapies, or surgical intervention. There also exists a need for treatments that can improve the irritative storage and/or obstructive voiding symptoms of LUTS without the risks and side effects of conventional drug therapies, or surgical intervention.

Throughout this description, including the foregoing description of related art, any and all publicly available documents described herein, including any and all U.S. patent published patent applications, are specifically incorporated by reference herein in their entirety. The foregoing description of related art is not intended in any way as an admission that any of the documents described therein, including pending U.S. patent applications, are prior art to the present disclosure. Moreover, the description herein of any disadvantages associated with the described products, methods, and/or apparatus, is not intended to limit the embodiments. Indeed, aspects of the embodiments may include certain features of the described products, methods, and/or apparatus without suffering from their described disadvantages.

SUMMARY OF THE EMBODIMENTS

There remains a need in the art for new, less toxic, and less frequent (e.g., avoiding the need to take medications daily or weekly) treatments for improving the quality of life for patients having LUTS. There also remains a need in the art for such treatments that improve irritative storage and/or obstructive voiding symptoms in patients with LUTS. The embodiments satisfy these needs.

This disclosure is premised in part on the discovery that certain peptides, including a specific peptide described by the amino acid sequence Ile-Asp-Gln-Gln-Val-Leu-Ser-Arg-Ile-Lys-Leu-Glu-Ile-Lys-Arg-Cys-Leu, (Fexapotide Triflutate or "FT") are capable of significantly improving lower urinary tract symptoms (LUTS), and more particularly improving irritative storage and/or obstructive voiding symptoms in patients with LUTS. This disclosure also is premised in part on the discovery that certain methods of administration of FT provide enhanced therapeutic efficacy of FT in treating LUTS-related disorders. Specifically, the embodiments include methods of enhancing the therapeutic efficacy of FT by administering compositions containing FT at least twice over a period of time in which the method of administering X amount of FT at least twice is more effective than administering a single dose of FT in an amount of 1×, 2×, or 4×. More particularly, the embodiments include methods of enhancing the therapeutic efficacy of FT by first administering FT, and subsequently administering FT at least one more time at least one year after the first administration.

The compositions can be administered intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transrectally, transperitoneally, transdermally, via an aerosol, infusion, bolus injection, implantation device, sustained release system etc. Alternatively, the FT peptide can be expressed in vivo by administering a gene that expresses the peptide, by administering a vaccine that induces such production or by introducing cells, bacteria or viruses that express the peptide in vivo, because of genetic modification or otherwise.

Another embodiment includes a method of improving nocturia by administering a composition comprising X amount of FT at least twice over a period of at least one year, wherein the method provides an increase in nocturia mean frequency change from baseline greater than the increase in nocturia mean frequency change from baseline achieved by administering only once a composition comprising 1× and 2× the amount of FT.

Another embodiment includes a method of improving the urinary peak flow rate (Qmax) mean change from baseline by administering a composition comprising X amount of FT at least twice over a period of at least one year, wherein the method provides an increase in the urinary peak flow rate (Qmax) mean change from baseline greater than the urinary peak flow rate (Qmax) mean change from baseline achieved by administering only once a composition comprising 2× and/or 4× the amount of FT.

Another embodiment includes a method of inhibiting the urinary flow worsening/obstruction as measured by the inability to provide a urine volume>125 ml (regardless of volume of prior water oral intake) by administering a composition comprising X amount of FT at least twice over a period of at least one year, wherein the method inhibits urinary flow worsening/obstruction in an amount greater than the inhibition achieved by administering only once a composition comprising 2× and 4× the amount of FT.

Both the foregoing general description and the following detailed description are exemplary and explanatory and are intended to provide further explanation of the embodiments as claimed. Other objects, advantages, and features will be readily apparent to those skilled in the art from the following detailed description of the embodiments.

DETAILED DESCRIPTION OF THE PREFERRED EMBODIMENTS

Before the embodiments are described, it is understood that this invention is not limited to the particular methodology, protocols, cell lines, vectors, and reagents described, as these may vary. It also is to be understood that the terminology used herein is for the purpose of describing particular embodiments only, and is not intended to limit the scope of the present embodiments which will be limited only by the appended claims.

Terms and phrases used herein are defined as set forth below unless otherwise specified. Throughout this description, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Amino acids and amino acid residues described herein may be referred to according to the accepted one or three-letter code provided in the table below.

TABLE 1

| Three-Letter Amino Acid | One-Letter Symbol | Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

Fexapotide Triflutate ("FT"), as it is used herein, denotes a 17-mer peptide having the amino acid sequence: Ile-Asp-Gln-Gln-Val-Leu-Ser-Arg-Ile-Lys-Leu-Glu-Iie-Lys-Arg-Cys-Leu (SEQ ID NO. 1). FT is disclosed in U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031. The disclosures of these patents and published applications are incorporated by reference herein in their entirety.

FT is represented by:

```
SEQ ID NO. 1:
IDQQVLSRIKLEIKRCL or Ile-Asp-Gln-Gln-Val-Leu-

Ser-Arg-Ile-Lys-Leu-Glu-Ile-Lys-Arg-Cys-Leu.
```

The term "fragment" refers to a protein or polypeptide that consists of a continuous subsequence of the amino acid sequence of a protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker. A person having ordinary skill in the art will be capable of selecting a suitable fragment for use in the embodiments without undue experimentation using the guidelines and procedures outlined herein.

The term "variant" refers to a protein or polypeptide in which one or more amino acid substitutions, deletions, and/or insertions are present as compared to the amino acid sequence of an protein or peptide and includes naturally occurring allelic variants or alternative splice variants of an protein or peptide. The term "variant" includes the replacement of one or more amino acids in a peptide sequence with a similar or homologous amino acid(s) or a dissimilar amino acid(s). There are many scales on which amino acids can be ranked as similar or homologous. (Gunnar von Heijne, Sequence Analysis in Molecular Biology, p. 123-39 (Academic Press, New York, N.Y. 1987.) Preferred variants include alanine substitutions at one or more of amino acid positions. Other preferred substitutions include conservative substitutions that have little or no effect on the overall net charge, polarity, or hydrophobicity of the protein. Conservative substitutions are set forth in Table 2 below.

TABLE 2

| Conservative Amino Acid Substitutions | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | praline |
| | methionine |
| | leucine |
| | isoleucine |

Table 3 sets out another scheme of amino acid substitution:

TABLE 3

| Original Residue | Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | eu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site (s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. For example, a cysteine residue may be added at both the amino and carboxy terminals of FT in order to allow the cyclisation of the peptide by the formation of a di-sulphide bond. The term "variant" also encompasses polypeptides that have the amino acid sequence of FT with at least one and up to 25 or more additional amino acids flanking either the 3' or 5' end of the peptide.

The term "derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to wild-type proteins or FT. Derivatives include salts. Such chemical modifications are well described in basic texts and in more detailed monographs, as well as in a voluminous research literature, and they are well known to those of skill in the art. It will be appreciated that the same type of modification may be present in the same or varying degree at several sites in a given protein or polypeptide. Also, a given protein or polypeptide may contain many types of modifications. Modifications can occur anywhere in a protein or polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, Proteins—Structure And Molecular Properties, 2nd Ed., T. E. Creighton, W. H. Freeman and Company, New York (1993) and Wold, F., "Posttranslational Protein Modifications: Perspectives and Prospects," pgs. 1-12 in Post-translational Covalent Modification Of Proteins, B. C. Johnson, Ed., Academic Press, New York (1983); Seifter et al., Meth. Enzymol. 182:626-646 (1990) and Rattan et al., "Protein Synthesis: Posttranslational Modifications and Aging," Ann. N.Y. Acad. Sci. 663: 48-62 (1992). The term "derivatives" include chemical modifications resulting in the protein or polypeptide becoming branched or cyclic, with or without branching. Cyclic, branched and branched circular proteins or polypeptides may result from post-translational natural processes and may be made by entirely synthetic methods, as well.

The term "homologue" refers to a protein that is at least 60 percent identical in its amino acid sequence of FT as determined by standard methods that are commonly used to compare the similarity in position of the amino acids of two polypeptides. The degree of similarity or identity between two proteins can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M Stockton Press, New York, 1991; and Carillo H. and Lipman, D., SIAM, J. Applied Math., 48:1073 (1988). Preferred methods to determine identity are designed to give the largest match between the sequences tested. Methods to determine identity and similarity are codified in publicly available computer programs.

Preferred computer program methods useful in determining the identity and similarity between two sequences include, but are not limited to, the GCG program package (Devereux, J., et al., Nucleic Acids Research, 12(1): 387 (1984)), BLASTP, BLASTN, and FASTA, Atschul, S. F. et al., J. Molec. Biol., 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol., 215:403-410 (1990). By way of example, using a computer algorithm such as GAP (Genetic Computer Group, University of Wisconsin, Madison, Wis.), the two proteins or polypeptides for which the percent sequence identity is to be determined are aligned for optimal matching of their respective amino acids (the "matched span", as determined by the algorithm).

A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al. in: Atlas of Protein Sequence and Structure, vol. 5, supp. 3 for the PAM250 comparison matrix; see Henikoff et al., Proc. Natl. Acad. Sci USA, 89:10915-10919 for the BLOSUM 62 comparison matrix) also may be used by the algorithm. The percent identity then is calculated by the algorithm. Homologues will typically have one or more amino acid substitutions, deletions, and/or insertions as compared with the comparison protein or peptide, as the case may be.

The term "fusion protein" refers to a protein where one or more peptides are recombinantly fused or chemically conjugated (including covalently and non-covalently) to a protein such as (but not limited to) an antibody or antibody fragment like an Fab fragment or short chain Fv. The term "fusion protein" also refers to multimers (i.e. dimers, trimers, tetramers and higher multimers) of peptides. Such multimers comprise homomeric multimers comprising one peptide, heteromeric multimers comprising more than one peptide, and heteromeric multimers comprising at least one peptide and at least one other protein. Such multimers may be the result of hydrophobic, hyrdrophilic, ionic and/or covalent associations, bonds or links, may be formed by cross-links using linker molecules or may be linked indirectly by, for example, liposome formation.

The term "peptide mimetic" or "mimetic" refers to biologically active compounds that mimic the biological activity of a peptide or a protein but are no longer peptidic in chemical nature, that is, they no longer contain any peptide bonds (that is, amide bonds between amino acids). Here, the term peptide mimetic is used in a broader sense to include molecules that are no longer completely peptidic in nature, such as pseudo-peptides, semi-peptides and peptoids. Examples of peptide mimetics in this broader sense (where part of a peptide is replaced by a structure lacking peptide bonds) are described below. Whether completely or partially non-peptide, peptide mimetics according to the embodiments provide a spatial arrangement of reactive chemical moieties that closely resemble the three-dimensional arrangement of active groups in the peptide on which the peptide mimetic is based. As a result of this similar active-site geometry, the peptide mimetic has effects on biological systems that are similar to the biological activity of the peptide.

The peptide mimetics of the embodiments are preferably substantially similar in both three-dimensional shape and biological activity to the peptides described herein. Examples of methods of structurally modifying a peptide known in the art to create a peptide mimetic include the inversion of backbone chiral centers leading to D-amino acid residue structures that may, particularly at the N-terminus, lead to enhanced stability for proteolytical degradation without adversely affecting activity. An example is given in the paper "Tritriated D-ala.sup.1-Peptide T Binding", Smith C. S. et al., Drug Development Res., 15, pp. 371-379 (1988). A second method is altering cyclic structure for stability, such as N to C interchain imides and lactames (Ede et al. in Smith and Rivier (Eds.) "Peptides: Chemistry and Biology", Escom, Leiden (1991), pp. 268-270). An example of this is given in conformationally restricted thymopentin-like compounds, such as those disclosed in U.S. Pat. No. 4,457,489 (1985), Goldstein, G. et al., the disclosure of which is incorporated by reference herein in its entirety. A third method is to substitute peptide bonds in the peptide by pseudopeptide bonds that confer resistance to proteolysis.

A number of pseudopeptide bonds have been described that in general do not affect peptide structure and biological activity. One example of this approach is to substitute retro-inverso pseudopeptide bonds ("Biologically active retroinverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the amino acid sequences of the peptides may be identical to the sequences of an peptide described above, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), Int. J. Peptide Protein Res., 41:181-184, incorporated herein by reference in its entirety).

Thus, the amino acid sequences of these peptides may be otherwise identical to the sequence of FT, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

Peptoid derivatives of peptides represent another class of peptide mimetics that retain the important structural determinants for biological activity, yet eliminate the peptide bonds, thereby conferring resistance to proteolysis (Simon, et al., 1992, Proc. Natl. Acad. Sci. USA, 89:9367-9371, incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the peptides may be replaced with the N-substituted glycine corresponding to the replaced amino acid.

The term "peptide mimetic" or "mimetic" also includes reverse-D peptides and enantiomers as defined below.

The term "reverse-D peptide" refers to a biologically active protein or peptide consisting of D-amino acids arranged in a reverse order as compared to the L-amino acid sequence of an peptide. Thus, the carboxy terminal residue of an L-amino acid peptide becomes the amino terminal for the D-amino acid peptide and so forth. For example, the peptide, ETESH, becomes $H_dS_dE_dT_dE_d$, where $E_d$, $H_d$, $S_d$, and $T_d$ are the D-amino acids corresponding to the L-amino acids, E, H, S, and T respectively.

The term "enantiomer" refers to a biologically active protein or peptide where one or more the L-amino acid residues in the amino acid sequence of an peptide is replaced with the corresponding D-amino acid residue(s).

A "composition" as used herein, refers broadly to any composition containing FT and, optionally an additional active agent. The composition may comprise a dry formulation, an aqueous solution, or a sterile composition. Compositions comprising FT may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

In an embodiment in which an additional active agent is used together with FT, the expression "active agent" is used to denote any agent that provides a therapeutic effect to a subject in need, and preferably is an agent capable of removing unwanted cellular proliferations and/or tissue growth. Suitable active agents may include, but are not limited to: (i) anti-cancer active agents (such as alkylating agents, topoisomerase I inhibitors, topoisomerase II inhibitors, RNA/DNA antimetabolites, and antimitotic agents); (ii) active agents for treating benign growths such as anti-acne and anti-wart active agents; (iii) antiandrogen compounds, (cyproterone acetate (1α, 2ß-methylene-6-chloro-17 α-acetoxy-6-dehydroprogesterone) Tamoxifen, aromatase inhibitors); (iv) alpha1-adrenergic receptor blockers (tamsulosin, terazosin, doxazosin, prazosin, bunazosin, indoramin, alfulzosin, silodosin); (v) 5 α-reductase inhibitors (finasteride, dutasteride); (vi) phosphodiesterase type 5 (PDE5) inhibitors (tadalafil) and combinations thereof.

Throughout this disclosure, the terms "obstructive" and "voiding" symptoms, and the terms "irritative" and "storage" systems, each as they refer to symptoms of patients having LUTS, are used interchangeably. The European Association of Urology (EAU) and American Urological Association (AUA) guidelines define LUTS as storage (irritative) symptoms (daytime urinary frequency, urgency, and nocturia), voiding (obstructive) symptoms (straining, weak stream, intermittent stream, and incomplete emptying), or postmicturition symptoms (postmicturition dribbling) that affect the lower urinary tract (LUT). Park, H. J., et al., "Urinary Tract Symptoms (LUTS) Secondary to Benign Prostatic Hyperplasia (BPH). *World J. Mens Health*, No. 31(3), 193-207 (2013).

Improvements in obstructive and irritative symptoms can be measured in accordance with techniques known in the art. For example, uroflowmeters are known to differentiate urine weight change to provide a continuous plot of the flow rate vs. time that is smoothed by internal electronic filtering to permit precise (±5%) measurement of Qmax. Schafer W, et al. "Good urodynamic practices: Uroflowmetry, filling cystometry and pressure-flow studies," *Neurourol Urodynamics*, Vol. 21, pp. 261-74 (2002). Nocturia can be measured in a variety of manners, most of which involve patients completing a questionnaire before and after treatment to establish a baseline, and then determine the difference (improvement, lack of improvement, worsening, etc.) from baseline after treatment. Exemplary questionnaires include evaluating the scores from the nocturia question included in the International Prostate Symptom Score (IPSS), assessing the number of nocturnal voids (Boyarsky symptom score), the Madsen-Iversen Symptom Score, and the ICSmale questionnaire. See, e.g., Chartier-Kastler, et al., "The Measurement of Nocturia and its Impact on Quality of Sleep and Quality of Life in LUTS/BPH," *Eur. Urol. Supp.*, Vol. 5, pp. 3-11 (2006). A preferred method of measuring nocturia is by determining the mean change from baseline of the nocturia question in the IPSS (question 7). Question 7 solicits from the patient how many times over the past month he had to get up to urinate from the time he went to bed until the time he got up—the score ranging from none (score 0) to 5 or more times (score 5).

Identifying patients with irritative and/or obstructive LUTS typically is carried out by a licensed and experienced medical professional, and is a separate diagnosis from benign prostatic hyperplasia (BPH). That is, while there is some overlap, patients having BPH do not necessarily also have LUTS, and patients having LUTS do not necessarily also have BPH. There are numerous techniques known in the art available for identifying patients having either irritative or obstructive LUTS. For example, Chapple, et al., MALE LOWER URINARY TRACT SYMPTOMS (LUTS), *An International Consultation on Male LUTS*, Fukuoka, Japan, Sep. 30-Oct. 4, 2012, Société Intematinoal d'Urologie, (2013), discloses established techniques for identifying patients suffering from obstructive symptoms (see, "Patient Assessment," Committee 2, Section 2.3, pp. 61-80 (103-122)), and for identifying patients suffering from Nocturia (see, "Assessment," Committee 3, Section 3.6, pp. 155-162 (197-204)). A person having ordinary skill in the art will be capable of identifying patients having obstructive LUTS, as well as patients having Nocturia, using the guidelines described herein, as well as those in the published literature disclosed herein.

While not intending on being bound by any particular theory or operation, the inventor unexpectedly discovered that administration of FT to a mammal at least twice spanning at least one year between the first administration and the at least second administration, provided an unexpectedly superior improvement in irritative and/or obstructive symptoms in patients with LUTS. The inventor unexpectedly discovered that such administration of FT provided unexpectedly superior improved symptoms in patients having LUTS, including both irritative and obstructive voiding symptoms, when compared to patients that were administered only a single dose of FT. The patients with LUTS may also have BPH, or in one embodiment, the patients with LUTS do not also have BPH. It will be understood that the population of patients who have LUTS and also have BPH is a subset of the overall patient population suffering from BPH. Consequently, methods of treating or ameliorating BPH do not necessarily also ameliorate irritative and/or obstructive symptoms in patents with LUTS.

Modest improvements in the inhibition of the progression of urinary flow worsening were found in patients given a single dose of FT 2.5 mg after 3 months but these improvements were not significantly better than control groups. Subjects given double the 2.5 mg single dose (two 2.5 mg doses) or 4× the dosage (four 2.5 mg doses) did not have significantly better response than single dose 2.5 mg. The inventor unexpectedly found that subjects who were given the same total dose (e.g., 5 mg) but with the dosage provided as 2 single dosages of e.g., 2.5 mg separated by >1 year had a significantly better inhibition of their progression of urinary flow worsening than the one-time administration of the double (5.0 mg) or quadruple (10.0 mg) dose.

Enhanced efficacy can be measured by determining the percent difference between the improvement achieved in accordance with the methods described herein, and the improvement achieved by a single administration. Those skilled in the art will appreciate that an improvement may be a higher or lower number, depending on the desired effect. For purposes of illustration, if administration of X amount of FT twice spanning at least year results in patients exhibiting a failure percentage of 5% (a lower number is better in this scenario), and administration of 2× of FT at the same time (e.g., 2 doses of X amount of FT) results in patients exhibiting a failure percentage of 15%, then the enhanced efficacy would be a 66.7% enhancement (((15−5)/15) *100%).

In accordance with one embodiment, the inventor discovered that methods described herein for administering FT provided an enhanced efficacy in reducing the percentage of patients with LUTS from urinary flow worsening/obstruction as measured by the percentage of patients exhibiting an inability to provide urine volume>125 ml regardless of volume of prior water intake (Qmax), of at least 50%, or from about 50% to about 100%, or from about 60% to about 95%, or from about 65% to about 85%, or from about 70% to about 80%, or any value therein, when compared to the control. In this embodiment, the enhanced efficacy when compared to a single administration of the same total amount of FT was more than 75%, or from about 81% to about 85%, and the enhanced efficacy when compared to a single administration of twice the same total amount of FT was greater than 80%, or from about 82% to about 85%.

In accordance with another embodiment, the inventor discovered that methods described herein for administering FT provided an enhanced efficacy in urinary flow improvement, measured by the peak flow rate (Qmax) mean change from baseline, of greater than about 75%, or from about 90% to about 200%, or from about 95% to about 150%, or from about 100% to about 120%, or from about 105% to about 115%, or any value therein, when compared to the control.

The inventor also discovered that methods described herein provided an enhanced efficacy in urinary flow improvement of greater than about 85%, or from about 95% to about 105%, when compared to a single administration of the same total amount of FT, and greater than about 30%, or from about 40% to about 50%, when compared to a single administration of twice the same total amount of FT.

In accordance with one embodiment, the inventor discovered that methods described herein for administering FT provided an enhanced efficacy in nocturia mean frequency change from baseline of greater than about 25%, or from about 35% to about 75%, or from about 40% to about 60%, or from about 42% to about 55%, or from about 45% to about 50%, or any value therein, when compared to the control. The inventor also discovered that methods described herein provided an enhanced efficacy in nocturia mean frequency change from baseline of greater than about 10%, or from about 15% to about 25%, when compared to a single administration of the same total amount of FT, and greater than about 25%, or from about 35% to about 40%, when compared to a single administration of ½ the total amount of FT.

The embodiments include a method of enhancing the therapeutic efficacy of compositions comprising FT in treating a mammal having BPH and having either irritative or obstructive (or both) LUTS, comprising first administering a composition including FT, and subsequently administering FT at least one more time at least one year after the first administration. The compositions may include FT as the sole active, or FT may be administered in combination with an additional active agent. The method includes, but is not limited to, administering a composition comprising FT intramuscularly, orally, intravenously, intraperitoneally, intracerebrally (intraparenchymally), intracerebroyentricularly, intralesionally, intraocularly, intraarterially, intrathecally, intratumorally, intranasally, topically, transdermally, subcutaneously, intradermally, transrectally, transperitoneally, either alone or conjugated to a carrier. The embodiments may optionally include first identifying patients with BPH that also are suffering from irritative and/or obstructive LUTS, and then administering the composition(s) comprising FT in accordance with the administration protocols described herein.

Any mammal can benefit from use of the invention, including humans, mice, rabbits, dogs, sheep and other livestock, any mammal treated or treatable by a veterinarian, zoo-keeper, or wildlife preserve employee. Preferred mammals are humans, sheep, and dogs. Throughout this description mammals and patients are used interchangeably.

It will be apparent to one of skill in the art that other smaller fragments of FT may be selected such that these peptides will possess the same or similar biological activity. Other fragments of FT may be selected by one skilled in the art such that these peptides will possess the same or similar biological activity. The term "FT" as used in the embodiments therefore encompasses these other fragments. In general, the peptides of the embodiments have at least 4 amino acids, preferably at least 5 amino acids, and more preferably at least 6 amino acids.

The embodiments also encompass methods of treatment comprising administering a composition comprising FT that includes two or more FT sequences joined together, together with an additional active agent. To the extent that FT has the desired biological activity, it follows that two or more FT sequences would also possess the desired biological activity.

FT and fragments, variants, derivatives, homologues, fusion proteins and mimetics thereof encompassed by this embodiment can be prepared using methods known to those of skill in the art, such as recombinant DNA technology, protein synthesis and isolation of naturally occurring peptides, proteins, variants, derivatives and homologues thereof. FT and fragments, variants, derivatives, homologues, fusion proteins and mimetics thereof can be prepared from other peptides, proteins, and fragments, variants, derivatives and homologues thereof using methods known to those having skill in the art. Such methods include (but are not limited to) the use of proteases to cleave the peptide, or protein into FT. Any method disclosed in, for example, U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031, can be used to prepare the FT peptide described herein. The disclosures of these patent documents are incorporated by reference herein in their entireties.

The additional active agent, if used, can be one or more active agents selected from (i) anti-cancer active agents (such as alkylating agents, topoisomerase I inhibitors, topoisomerase II inhibitors, RNA/DNA antimetabolites, and antimitotic agents); (ii) active agents for treating benign growths such as anti-acne and anti-wart active agents (salicylic acid); (iii) antiandrogen compounds, (cyproterone acetate (1α, 2ß-methylene-6-chloro-17 α-acetoxy-6-dehydroprogesterone)) Tamoxifen, aromatase inhibitors); (iv) alpha1-adrenergic receptor blockers (tamsulosin, terazosin, doxazosin, prazosin, bunazosin, indoramin, alfulzosin, silodosin); (v) 5 α-reductase inhibitors (finasteride, dutasteride); (vi) phosphodiesterase type 5 (PDE5) inhibitors (tadalafil) and combinations thereof. Preferably, the additional active agent is selected from the group consisting of tamsulosin, finasteride, terazosin, doxazosin, prazosin, tadalafil, alfuzosin, silodosin, dutasteride, combinations of dutasteride and tamsulosin, and mixtures and combinations thereof.

Therapeutic compositions described herein may comprise an amount of FT in admixture with a pharmaceutically acceptable carrier. In some alternative embodiments, the additional active agent can be administered in the same composition with FT, and in other embodiments, the composition comprising FT is administered as an injection, whereas the additional active agent is formulated into an oral medication (gel, capsule, tablet, liquid, etc.). The carrier material may be water for injection, preferably supplemented with other materials common in solutions for administration to mammals. Typically, FT will be administered in the form of a composition comprising the purified FT peptide (or chemically synthesized FT peptide) in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Compositions of the embodiments also may comprise buffers known to those having ordinary skill in the art with an appropriate range of pH values, including Tris buffer of about pH 7.0-8.5, or acetate buffer of about pH 4.0-5.5, which may further include sorbitol or a suitable substitute therefor.

Solid dosage forms for oral administration include but are not limited to, capsules, tablets, pills, powders, and granules. In such solid dosage forms, the additional active agent, and/or FT can be admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alginates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as acetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the compositions of the embodiments may be varied to obtain an amount of FT and additional active agent that is effective to obtain a desired therapeutic response for a particular composition. The selected dosage level therefore depends upon the desired therapeutic effect, the route of administration, the desired duration of treatment, and other factors.

With mammals, including humans, the effective amounts can be administered on the basis of body surface area. The interrelationship of dosages for animals of various sizes, species and humans (based on mg/M² of body surface) is described by E. J. Freireich et al., Cancer Chemother. Rep., 50 (4):219 (1966). Body surface area may be approximately determined from the height and weight of an individual (see e.g., Scientific Tables, Geigy Pharmaceuticals, Ardsley, N.Y. pp. 537-538 (1970)).

It will be understood that the specific dose level for any particular patient will depend upon a variety of factors including the body weight, general health, sex, diet, time and route of administration, potency of the administered drug, rates of absorption and excretion, combination with other drugs and the severity of the particular disease being treated. It is preferred that the composition is administered at least twice in which the at least second administration occurs at least one year after the first administration. In this embodiment, the period of time between administration of the composition may vary anywhere from 1 year to 15 years, or from 1 year to 4 years, or between 1 and 2 years.

A method of administering a composition comprising FT according to the embodiments includes, but is not limited to, administering the compositions intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transrectally, transperitoneally, transdermally, via an aerosol, infusion, bolus injection, implantation device, sustained release system etc. Any method of administration disclosed in, for example, U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031, can be used.

In certain embodiments, the FT peptide can be administered in combination with at least one active agent selected from the group consisting of (1) of an inhibitor of 5α-reductase and/or an antiestrogen, (2) an inhibitor of 5α-reductase and/or an aromatase inhibitor, (3) a 5α-reductase inhibitor and/or a 17β-HSD inhibitor, (4) a 5α-reductase inhibitor, an antiestrogen and an aromatase inhibitor, (5) a 5α-reductase inhibitor, an antiestrogen and a 17β-HSD inhibitor, (6) a 5α-reductase inhibitor, an aromatase inhibitor, an antiestrogen and a 17β-HSD inhibitor, (7) a 5α-reductase inhibitor, an antiandrogen and an antiestrogen, (8), a 5α-reductase inhibitor, an antiandrogen and an aromatase inhibitor, (9) a 5α-reductase inhibitor, an antiandrogen and an 17β-HSD inhibitor, (10) a 5α-reductase inhibitor, an antiandrogen, an antiestrogen and an aromatase inhibitor, (11) a 5α-reductase inhibitor, an antiandrogen, an aromatase inhibitor and a 17β-HSD inhibitor, (12) a 5α-reductase inhibitor, an antiandrogen, an aromatase inhibitor, an antiestrogen and a 17β-HSD inhibitor, (13) a 17β-HSD inhibitor and an antiestrogen, (14) a 17β-HSD inhibitor and an aromatase inhibitor, (15) a 17β-HSD inhibitor, an aromatase inhibitor and an antiestrogen, (16) a 17β-HSD inhibitor, an antiandrogen and an antiestrogen, (17) a 17β-HSD inhibitor, an antiandrogen and an aromatase inhibitor, (18) a 17β-HSD inhibitor, an antiandrogen, an antiestrogen and an aromatase inhibitor, (19) an antiestrogen and an aromatase inhibitor and (20) an antiestrogen, an aromatase inhibitor, and an antiandrogen, (21) an LHRH agonist or antagonist, an inhibitor of 5α-reductase and an antiestrogen, (22) an LHRH agonist or antagonist, an inhibitor of 5α-reductase and an aromatase inhibitor, (23) an LHRH agonist or antagonist, a 5 reductase inhibitor and a 17β-HSD inhibitor, (24) an LHRH agonist or antagonist, a 5α-reductase inhibitor, an antiestrogen and an aromatase inhibitor, (25) an LHRH agonist or antagonist, a 5α-reductase inhibitor, an antiestrogen and a 17β-HSD inhibitor, (26) an LHRH agonist or antagonist, a 5α-reductase inhibitor, an aromatase inhibitor, an antiestrogen and a 17β-HSD inhibitor, (27) an LHRH agonist or antagonist, a 5α-reductase inhibitor, an antiandrogen and an antiestrogen, (28), an LHRH agonist or antagonist, a 5α-reductase inhibitor, an antiandrogen and an aromatase inhibitor, (29) an LHRH agonist or antagonist, a 5α-reductase inhibitor, an antiandrogen and an 17β-HSD inhibitor, (30) an LHRH agonist or antagonist, a 5α-reductase inhibitor, an antiandrogen, an antiestrogen and an aromatase inhibitor, (31) an LHRH agonist or antagonist, a 5α-reductase inhibitor, an antiandrogen, an aromatase inhibitor and a 17β-HSD inhibitor, (32) an LHRH agonist or antagonist, a 5α-reductase inhibitor, an antiandrogen, an aromatase inhibitor, an antiestrogen and a 17β-HSD inhibitor, (33) an LHRH agonist or antagonist, a 17β-HSD inhibitor and an antiestrogen, (34) an LHRH agonist or antagonist, a 17β-HSD inhibitor and an aromatase inhibitor, (35) an LHRH agonist or antagonist, a 17β-HSD inhibitor, an aromatase inhibitor and an antiestrogen, (36) an LHRH agonist or antagonist, a 17β-HSD inhibitor, an antiandrogen and an antiestrogen, (37) an LHRH agonist or antagonist, a 17β-HSD inhibitor, an antiandrogen and an aromatase inhibitor, (38) an LHRH agonist or antagonist, a 17β-HSD inhibitor, an antiandrogen, an antiestrogen and an aromatase inhibitor,

(39) an LHRH agonist or antagonist, an antiestrogen and an aromatase inhibitor and (40) an LHRH agonist or antagonist, an antiestrogen, an aromatase inhibitor, and an antiandrogen.

FT is a new molecular entity which in vitro stimulates caspase pathways (activation of caspases 7, 8, and 10, caspase recruitment domains 6, 11, and 14, and DIABLO), tumor necrosis factor pathways (activation of TNF1, TNFSF6, TNFSF8, TNFSF9, CD70 ligands, and TNFRSF19L, TNFRSF25, TRAF2, TRAF3, TRAF4, TRAF6 receptors), and BCL pathways (activation of BIK, HRK, BCL2L10 and BCL3) in prostate glandular epithelial cells, based on tissue culture genetic array data. FT selectively causes loss of cell membrane integrity, mitochondrial metabolic arrest, depletion of RNA, DNA lysis and aggregation, and cell fragmentation and cell loss. The apoptotic process leads to typical ultrastructural progressive changes of membranous disruption and swelling, progressively deepening nuclear invaginations with eventual membranous bleb formations and cell death and fragmentation into apoptotic bodies. Histologically, typical apoptotic changes with positive immunohistochemical staining of markers for apoptosis are found throughout the injected areas for up to several weeks after treatment.

FT has been extensively tested in patients with BPH and in men with low-grade (T1c) prostate cancer. The compound and placebo controls have been administered by the transrectal route in over 1700 procedures in 9 human clinical trials. In these large long-term clinical trials in men with BPH, FT was administered in a concentration of 0.25 mg/ml (2.5 mg of FT—amounting to administration to about 15-20% of the gland by volume). See, e.g., Shore, et al., "The potential for NX-1207 in benign prostatic hyperplasia: an update for clinicians," *Ther Adv. Chronic Dis.*, 2(6), pp. 377-383 (2011). It therefore is preferred that compositions comprising FT include 2.5 mg of FT, and that such compositions are administered at least twice over a period spanning at least one year. The inventor unexpectedly discovered that such administration of FT provided improvements in obstructive and voiding symptoms of LUTS exceeding those seen by administration of a single dose of 2.5 mg, a dose of 5.0 mg (2 doses of 2.5 mg given at the same time), a dose of 10.0 mg (4 doses of 2.5 mg given at the same time), and a placebo control.

The following examples are provided to illustrate the present embodiments. It should be understood, however, that the embodiments are not to be limited to the specific conditions or details described in these examples. Throughout the specification, any and all references to a publicly available document, including a U.S. patent, are specifically incorporated by reference. In particular, the embodiments expressly incorporate by reference the examples contained in U.S. Pat. Nos. 6,924,266; 7,241,738; 7,317,077; 7,408,021; 7,745,572; 8,067,378; 8,293,703; 8,569,446; and 8,716,247, and U.S. Patent Application Publication Nos. 2017/0360885; 2017/0020957; 2016/0361380; and 2016/0215031, each of which reveal that certain peptides specified therein are effective agents for causing cell death in vivo in normal rodent muscle tissue, subcutaneous connective tissue, dermis and other tissue.

EXAMPLES

Clinical trials were conducted on numerous individuals having BPH, some of whom also had LUTS. All protocols were done in accordance with applicable regulations, and carried out by physicians.

Example One

Patients with BPH and who optionally also had LUTS were given an intraprostatic injection of either a) FT 2.5 mg in phosphate buffered saline pH 7.2 ("PBS") or b) PBS alone, under double-blind conditions by a urologist in an office setting under ultrasound guidance. Patients were followed for >=3 months to several years with regular physical examinations, laboratory tests, and evaluations of symptoms. Urinary peak flow (Qmax) was measured by flow meter readings using standard techniques, at 3 months and at 12 months in subjects who were able to urinate adequate volume of urine (>125 mL) to provide a valid test. Subjects who were unable to void >=125 mL despite drinking as much water as they wanted were classified as "Qmax unable". The numbers of subjects who became Qmax unable was compared in different groups. Surprisingly, subjects who received 2 separate FT 2.5 treatments had significantly better responses than subjects who received the 2 dosage amount in one treatment of 5 mg, or the equivalent of 4 treatments in a 10 mg single dosage, or controls with single treatment FT 2.5 mg or vehicle alone treatment. The results from example 1 are provided in Table 4 below.

TABLE 4

% of Patients With Inability to Provide Urine Volume >125 mL

| Group | N | % of Patients (days after last treatment) |
|---|---|---|
| Single Dose of 5.0 mg FT | 33 | 21%* (90 days) |
| Single Dose of 10.0 mg FT | 30 | 23.3%** (90 days) |
| Two Doses of 2.5 mg FT > 1 year apart | 203 | 3.9% (180 days) |
| Placebo (Vehicle alone) | 36 | 16.7%*** (90 days) |

*p = 0.002 vs. 2-dose
**p = 0.001 vs. 2-dose
***p = 0.0027 vs. 2-dose

The results from Table 4 reveal that administering a composition comprising FT at least twice over a period spanning at least one year significantly reduced the percentage of patients with Qmax failures, when compared to the control (about 77% improvement), when compared to a single administration of twice the amount of a single administration of FT (about 81.4% improvement), and when compared to a single administration of four times the amount of a single administration of FT (about 83.3% improvement). The results from Table 4 also reveal that a single administration of twice the amount, and of four times the amount of FT used in the multiple administration regimen less effective in reducing the percentage of patients with Qmax failures when compared to the control. It therefore is entirely unexpected that administering FT twice to a patient over a period spanning more than one year would be capable of reducing the percentage of patients with Qmax failures by 81.4% when compared to the control, when single administrations of the same active in amounts double and quadruple the amount administered each time were less effective than the control.

Example Two

Patients with BPH and who optionally also had LUTS were given an intraprostatic injection of either a) FT 2.5 mg in 10 mL phosphate buffered saline pH 7.2 ("PBS") or b) FT 5.0 mg in PBS or c) FT 2.5 mg in PBS 2-dosages given >1 year apart, or d) PBS 10 mL alone, under double-blind conditions by a urologist in an office setting under ultrasound guidance. Patients were followed for >=3 months to several years with regular physical examinations, laboratory tests, and evaluations of symptoms. Urinary peak flow (Qmax) was measured by flow-meter readings using standard techniques, at 3 months and at 12 months or longer in subjects who were able to urinate adequate volume of urine (>125 mL) to provide a valid test. All peak flow measurements were assessed by a blinded central reader. The mean peak flow rate change from baseline was compared in different groups. Surprisingly, subjects who received 2 separate FT 2.5 treatments had significantly better responses than subjects who received the 2 dosage amount in one treatment of 5 mg, or the equivalent of 4 treatments in a 10 mg single dosage, or controls with single treatment vehicle alone treatment. The results from example 2 are provided in Table 5 below.

TABLE 5

Peak Flow Rate (Qmax) Mean Change From Baseline

| Group | N | Mean Change of Qmax (ml/sec) |
| --- | --- | --- |
| Single Dose of 5.0 mg FT | 33 | 1.28 |
| Single Dose of 10.0 mg FT | 30 | 1.76 |
| Two Doses of 2.5 mg FT > 1 year apart | 203 | 2.59 |
| Placebo (Vehicle alone) | 36 | 1.23 |

The results from Table 5 reveal that administering a composition comprising FT at least twice over a period spanning at least one year significantly improved the peak flow rate, as measured by a mean change from baseline, when compared to the control (about 111% improvement), when compared to a single administration of twice the amount of a single administration of FT (about 102% improvement), and when compared to a single administration of four times the amount of a single administration of FT (about 47% improvement).

Example Three

Patients with BPH and who optionally also had LUTS were given an intraprostatic injection of either a) FT2.5 in 10 mL phosphate buffered saline pH 7.2 ("PBS") or b) FT 5.0 mg in PBS or c) FT 2.5 mg in PBS 2-dosages given >1 year apart, or d) PBS 10 mL alone, under double-blind conditions by a urologist in an office setting under ultrasound guidance. Patients were followed for >=3 months to several years with regular physical examinations, laboratory tests, and evaluations of symptoms. The mean difference from baseline nocturia scores to follow-up scores (nocturia scores are the values provided to question #7 in the IPSS) were calculated in FT treated subjects given single dose FT 2.5 mg, single dose FT 0.5 mg, 2-dose 2.5 mg>1 year apart, and Placebo treated controls. Surprisingly, the amount of improvement (reduction) in nocturia mean frequency results in subjects who had >1 year apart repeat dosage of 2.5 mg reached statistical significance where the single higher dosages did not, even when the same total amount of FT was administered. The results from example 3 are provided in Table 6 below.

TABLE 6

Nocturia Score Mean Change From Baseline

| Group | N | Nocturia Score Mean Change |
| --- | --- | --- |
| Single Dose of 2.5 mg FT | 586 | −0.54 (SD 1.1)* |
| Single Dose of 5.0 mg FT | 37 | −0.62 (SD 1.64)* |
| Two Doses of 2.5 mg FT > 1 year apart | 203 | −0.74 (SD 1.26)**, *** |
| Placebo (Vehicle alone) | 391 | −0.50 (SD 1.1) |

*not significant vs. vehicle alone
**p = 0.012 vs. Vehicle alone
*** p = 0.03 vs. single dosage 2.5 mg.

The results from Table 6 reveal that administering a composition comprising FT at least twice over a period spanning at least one year provided an improved nocturia score mean change from baseline, when compared to the control, of about 48% improvement), of about 37%, when compared to a single administration of the same individual amount, and about 19.4%, when compared to a single administration of twice the individual amount.

The results from the afore-described examples provide surprising data for patients having BPH, and who may or may not also have LUTS. Thus, patients having BPH, but do not have LUTS would not necessarily experience the improved results provided in the examples. As a consequence, these patients would have been expected to skew the results less favorably because they would not necessarily exhibit any improvement in irritative and/or obstructive LUTS, when starting with a baseline of little to no irritative and/or obstructive LUTS. Accordingly, it is believed that identifying patients having BPH who also have LUTS, and then administering the compositions comprising FT to those patients in the manner described herein, would provide even greater improvement in: (a) reducing the percentage of Qmax failures; (b) improving the mean flow rate (Qmax) from baseline; and (c) improving Nocturia score mean change from baseline, than the improvements shown in the above Examples 1-3, respectively.

What is claimed is:

1. A method of enhancing the therapeutic efficacy of Fexapotide Triflutate (FT) in improving at least the urinary peak flow rate (Qmax) mean change from baseline and/or the urinary flow worsening/obstruction as measured by the inability to provide a urine volume>125 ml, comprising
    a) identifying and selecting patients having irritative or obstructive Lower Urinary Tract Symptoms (LUTS) LUTS;
    b) first administering a composition comprising FT to a patient identified and selected in (a) above; and
    c) subsequently administering a composition comprising FT to the patient at least more than one year after the first administration, thereby administering a total dosage of FT comprising the sum of the first and subsequent administrations of FT,
    wherein the method improves at least the urinary peak flow rate (Qmax) mean change from baseline and/or the urinary flow worsening/obstruction as measured by the inability to provide a urine volume>125 ml, in an amount greater than the respective improvement in patients that were administered the same total dosage of FT or twice the total dosage of FT in a single administration.

2. The method of claim 1, wherein the method comprises administration of Fexapotide Triflutate and a carrier.

3. The method of claim 1, wherein the method comprises administration of Fexapotide Triflutate in a concentration of 2.5 mg/L.

4. The method of claim 1, wherein Fexapotide Triflutate is administered by a method selected from the group consisting of orally, subcutaneously, intradermally, intranasally, intravenously, intramuscularly, intrathecally, intranasally, intratumorally, topically, transrectally, transperitoneally, and transdermally.

5. A method of enhancing the therapeutic efficacy of Fexapotide Triflutate (FT) in improving at least nocturia in patients having Lower Urinary Tract Symptoms (LUTS), comprising:
    a) identifying and selecting patients having irritative symptoms of LUTS;
    b) administering a first composition comprising Fexapotide Triflutate (FT) to a patient identified and selected in (a) above; and
    c) administering a second composition comprising FT to the patient at least more than one year after administering the first composition, thereby administering a total dosage of FT comprising the sum of the first and subsequent administrations of FT,
    wherein the method improves at least nocturia in an amount greater than the improvement in nocturia in patients that were administered the same total dosage of FT in a single administration.

6. The method of claim 5, wherein FT is present in the first composition in a concentration of about 2.5 mg/l.

7. The method of claim 6, wherein FT is present in the second composition in a concentration of about 2.5 mg/l.

8. A method of enhancing the therapeutic efficacy of Fexapotide Triflutate (FT) in treating obstructive symptoms of patients with Lower Urinary Tract Symptoms (LUTS), comprising:
    a) identifying and selecting patients having obstructive symptoms of LUTS;
    b) administering a first composition comprising Fexapotide Triflutate (FT) to a patient identified and selected in (a) above; and
    c) administering a second composition comprising FT to the patient at least more than one year after administering the first composition, thereby administering a total dosage of FT comprising the sum of the first and subsequent administrations of FT,
    wherein the method improves at least one obstructive symptom of LUTS in an amount greater than the respective improvement in patients that were administered the same total dosage of FT or twice the total dosage of FT in a single administration.

9. The method of claim 8, wherein the obstructive symptoms are selected from the group consisting of straining, weak stream, intermittent stream, and incomplete emptying.

10. The method of claim 8, wherein FT is present in the first composition in a concentration of about 2.5 mg/l.

11. The method of claim 10, wherein FT is present in the second composition in a concentration of about 2.5 mg/l.

12. The method of claim 8, wherein the method provides an improvement in peak flow rate (Qmax) mean change from baseline of from about 100% to about 200%, when compared to a placebo control.

13. The method of claim 8, wherein the method provides an improvement in peak flow rate (Qmax) mean change from baseline, of from about 95% to about 105%, when compared to administration of the same total amount of FT only once.

14. The method of claim 1, wherein the method provides an improvement in peak flow rate (Qmax) mean change from baseline, of from about 95% to about 105%, when compared to administration of the same total amount of FT only once.

* * * * *